Figure 1:
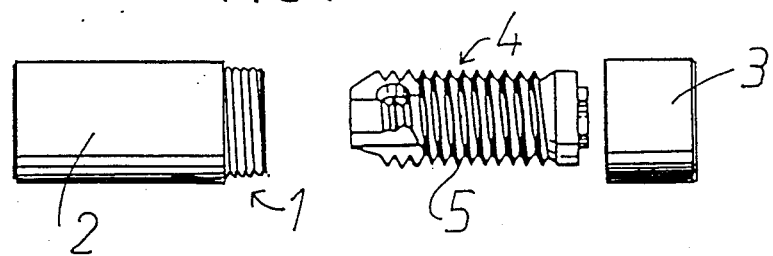

United States Patent [19]

Hansson et al.

[11] Patent Number: 4,671,410

[45] Date of Patent: Jun. 9, 1987

[54] PACKAGE FOR STERILE AND CONTAMINATION-FREE STORAGE OF ARTIFICIAL IMPLANTS

[75] Inventors: Stig Hansson, Askim; Einar Jörgensson, Hisings Kärra, both of Sweden

[73] Assignee: Nobelpharma Aktiebolag, Goteborg, Sweden

[21] Appl. No.: 813,354

[22] Filed: Dec. 26, 1985

[30] Foreign Application Priority Data

Dec. 27, 1984 [SE] Sweden .................................. 8406590

[51] Int. Cl.[4] ....................... B65D 81/08; B65D 81/18
[52] U.S. Cl. ................................. 206/438; 206/524.6; 206/591; 623/66
[58] Field of Search ...................... 128/68, 75; 206/5.1, 206/63.3, 63.5, 83, 363, 438–441, 514, 591, 593, 594, 524.6; 623/11, 12, 17, 57, 65, 66

[56] References Cited

U.S. PATENT DOCUMENTS

| | | | |
|---|---|---|---|
| 2,568,838 | 9/1951 | Wilcox | 206/83 |
| 4,423,732 | 1/1984 | Tarjan et al. | 206/438 |
| 4,512,471 | 4/1985 | Kaster et al. | 206/438 |
| 4,522,209 | 6/1985 | Patrick et al. | 206/438 |
| 4,588,085 | 5/1986 | Sussman | 206/438 |

Primary Examiner—William Price
Assistant Examiner—Jimmy G. Foster
Attorney, Agent, or Firm—Armstrong, Nikaido, Marmelstein & Kubovcik

[57] ABSTRACT

The invention relates to a package for sterile and contamination-free storage of artificial implants, comprising an inner capsule (1) to hold said implant (4) and being made of the same material as the implant, a hermetically sealed outer casing (6) surrounding said capsule (1) and a positioning member (7) arranged inside said outer casing (6) and in yielding abutment with the capsule (1).

7 Claims, 2 Drawing Figures

U.S. Patent    Jun. 9, 1987    4,671,410

PACKAGE FOR STERILE AND CONTAMINATION-FREE STORAGE OF ARTIFICIAL IMPLANTS

The present invention relates to a package of sterile and contaminationfree storage of artificial implants.

It is well known that the biocompatibility of an implant material is intimately associated with the surface properties of the material, i.e. the chemical composition, microstructure and so on of the surface layer. It is therefore of the utmost importance that the surface layer is carefully controlled and specified at atom level. Two implants manufactured initially from the same material can, for instance, acquire totally different biochemical properties depending on how the material is treated and the purification procedure employed when the implant is manufactured.

The package according to the present invention can be generally used for all types of artificial implants, instruments, etc. which can withstand sterilization temperatures. In the following the invention will be described as applied to titanium fixtures for implantation without, however, being limited thereto.

The high degree of biocompatibility of such titanium fixtures is intimately associated with the (oxide) surface formed at the manufacturing stage and subsequent treatment of these titanium fixtures. This special surface treatment is essential to ensure firm anchoring of the titanium fixture in the bone tissue when such fixtures are used, for instance, to provide attachment means for artificial teeth, dental bridges, prosthesis parts, etc. Since, therefore, the surface layer of the titanium fixture is of decisive significance for the implantation process aimed at, it must be guaranteed that this surface remains unaltered from manufacture to use.

Such titanium fixtures have previously been supplied in special boxes and then individually washed and sterilized prior to use, sterilization usually being performed in an autoclave. However, in practice it has been found that this known method has a number of drawbacks in that it is impractical for the user and especially that it is unsatisfactory from the cleanliness aspect. It has been found, for instance, that the surface layer of titanium fixtures stored and treated in this matter is altered in uncontrolled manner depending on the autoclave used for sterilization, the purity of the water, etc. In many cases major alterations in the surface layer of the implant can be observed which might jeopardize the implantation process.

There is therefore an acute need for a package for such titanium fixtures which guarantees that they are received by the user in a condition which will not jeopardize the subsequent implantation process. The demands placed on such a package are extremely high and are not fulfilled by any sterile package commercially available hitherto.

The object of the present invention is thus not only to fulfill the demands for sterility in conjunction with the artificial implants under consideration, but also to guarantee freedom from contamination right down to the atom/molecule level.

According to the invention it has now surprisingly proved possible to solve the problems described above and this is achieved in the package described in the introduction by an inner capsule to hold said implant and being made of the same material as the implant, a hermetically sealed outer casing surrounding said capsule and a positioning member arranged inside said outer casing and in yielding abutment with the capsule.

According to a suitable embodiment of the method according to the invention, sterilization is performed for 2–4 hours at a temperature of 160°–180° C. and may suitably be performed by means of dry sterilization in air or by means of sterilization in an autoclave.

According to a suitable embodiment of the invention the inner capsule is closable and the outer casing consists of a hermetically sealable glass container.

According to a suitable embodiment of the invention the positioning member comprises a spring, one end of which is arranged to abut one short side of the capsule and the other end of the spring is secured in the outer casing.

Further characteristics of the invention are revealed by the features defined in the accompanying claims.

Figure 2:
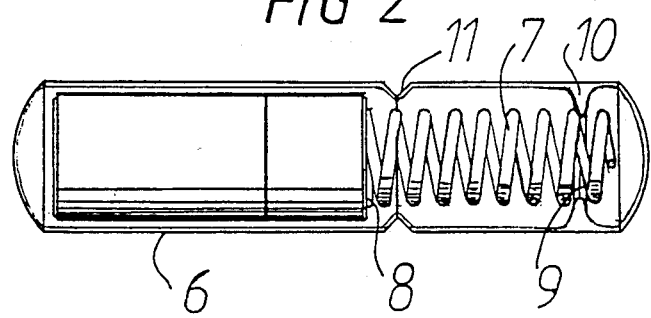

The invention will be described in more detail in the following with reference to a number of embodiments shown in the accompanying drawings in which, FIG. 1 shows a view of a closable capsule and FIG. 2 shows a view of a package according to the invention comprising an inner capsule and a hermetically sealed outer casing.

The capsule 1 shown in FIG. 1 consists of a cylindrical body 2 with screw-on lid 3. According to a preferred embodiment of the invention it is made of titanium. The titanium capsule 1 is designed to hold a titanium fixture 4. The titanium capsule 1 provides protection against mechanical damage and has the considerable advantage of ensuring that the titanium fixture 4 only comes into direct contact with titanium. The titanium capsule 1 shown in FIG. 1 is neither sterile nor tight-gas per se, however, and does not therefore protect the surface of the titanium fixture 5 from all types of impurities. According to the invention, therefore, the outer casing shown in FIG. 2 is used, here in the form of a glass ampoule which both maintains the sterility and protects the surface of the fixture 5 inside the titanium capsule 1 from impurities.

As is evident from FIG. 2, a positioning member 7 in the form of a spring is arranged inside the glass ampoule 6, its end 8 abutting the lid 3 of the titanium capsule 1. The other end 9 of the spring is suitably secured by means of a stud 10 protruding inwardly from the inner wall of the glass ampoule 6. The glass ampoule 6 is also provided with a fractural impression, known per se.

According to the invention a titanium fixture is packaged as follows:

1. The titanium fixture 4 is applied inside the titanium capsule 1. It is essential that the highest degree of cleanliness is observed in this step.
2. The titanium capsule 1 containing the titanium fixture 4 is enclosed in a tight outer casing 6 such as the glass ampoule shown in FIG. 2. The package thus obtained is sterilized by heating to 160°–180° C. for 2–4 hours. Alternatively a small quantity of water may be introduced into the capsule before it is sealed, in which case heating to autoclaving temperature is sufficient.

Before the package is broken when it is to be used, it should preferably be treated in an autoclave to sterilize its outer sides.

The outer casing used according to the invention should therefore permit vacuum-tight sealing to prevent any possible impurities from reaching the sensitive surfaces of the titanium fixture located in the titanium capsule. A vacuum-tight seal automatically more than fulfils the requirement of a sterile seal.

Another requirement is that the material, of which the outer casing is made, should not emit any form of impurity at the time of sealing or sterilization. At the same time the capsule is positioned inside the outer casing which is particularly important if the outer casing consists of a glass ampoule.

The package according to the invention is thus manufactured of the same material as the artificial implant. If, for instance, the capsule is to contain a titanium fixture, the capsule, its lid and even the positioning member should be made of titanium. If the capsule is to hold a stainless steel implant, the capsule and lid may be made of stainless steel material and so on.

If a different material is used for the capsule and for the implant there is a risk that the material of the capsule may rub off onto the implant or that microscopic quantities of the capsule may be transferred to the surface of the implant by vaporization.

The contents of the capsule is sterilized (free from contamination) after sealing by heating to 160°–180° C. This results in dry sterilization since the capsule is filled with air. Prior to clinical use, the outside of the capsule is sterilized in an autoclave together with instruments, etc.

If for some reason the implant is to be sterilized at a lower temperature than 160°–180° C. (or a moist atmosphere desired) a small, specified quantity of water may be added before the capsule is sealed, in which case heating to autoclaving temperature is sufficient.

We claim:

1. A package containing an artificial implant for sterile storage of the artificial implant, comprising an artificial implant (4), an inner capsule (1) to hold said implant and being made of the same material as the implant, a hermetically sealed outer casing (6) surrounding said capsule (1) and a positioning member (7) arranged inside said outer casing (6) and in yielding abutment with the capsule (1).

2. A package according to claim 1, wherein the inner capsule (1) is closable.

3. A package according to claim 1, wherein the outer casing (6) consists of a hermetically sealable glass container.

4. A package according to claim 3, wherein said glass container (6) consists of borosilicate glass (pyrex glass).

5. A package according to any one of claims 1–4, wherein the outer casing (6) is provided with a fracturable impression (11).

6. A package according to claim 5, wherein the positioning member (7) comprises a spring, one end (8) of which is arranged to abut one short side (3) of the capsule.

7. A package according to claim 6, wherein the other end (9) of the spring (7) is secured in the glass container (6).

* * * * *